(12) United States Patent
Addison et al.

(10) Patent No.: US 7,944,551 B2
(45) Date of Patent: May 17, 2011

(54) SYSTEMS AND METHODS FOR A WAVELET TRANSFORM VIEWER

(75) Inventors: Paul Stanley Addison, Edinburgh (GB); James Watson, Dunfermline (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 295 days.

(21) Appl. No.: 12/249,046

(22) Filed: Oct. 10, 2008

(65) Prior Publication Data

US 2009/0323049 A1    Dec. 31, 2009

Related U.S. Application Data

(60) Provisional application No. 61/077,072, filed on Jun. 30, 2008, provisional application No. 61/077,130, filed on Jun. 30, 2008.

(51) Int. Cl.
*A61B 5/1455* (2006.01)
(52) U.S. Cl. .......... 356/41; 600/323; 600/529; 702/189; 702/190
(58) Field of Classification Search .................... 356/41; 600/323, 529, 309, 310, 324, 502, 534; 702/189
See application file for complete search history.

(56) References Cited

U.S. PATENT DOCUMENTS

| | | | |
|---|---|---|---|
| 4,289,141 A | 9/1981 | Cormier | |
| 5,439,483 A | 8/1995 | Duong-Van | |
| 5,590,650 A | 1/1997 | Genova | |
| 5,632,272 A | 5/1997 | Diab et al. | |
| 5,774,597 A | 6/1998 | Wilson | |
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,967,995 A | 10/1999 | Shusterman et al. | |
| 6,002,952 A | 12/1999 | Diab et al. | |
| 6,036,653 A | 3/2000 | Baba et al. | |
| 6,094,592 A | 7/2000 | Yorkey | |
| 6,095,984 A | 8/2000 | Amano et al. | |
| 6,117,075 A | 9/2000 | Barnea | |
| 6,129,675 A | 10/2000 | Jay | |
| 6,135,966 A | 10/2000 | Ko | |
| 6,171,257 B1 | 1/2001 | Weil et al. | |
| 6,171,258 B1 | 1/2001 | Karakasoglu et al. | |
| 6,208,951 B1 | 3/2001 | Kumar et al. | |
| 6,293,915 B1 | 9/2001 | Amano et al. | |

(Continued)

FOREIGN PATENT DOCUMENTS

JP        09-084776        3/1997

(Continued)

OTHER PUBLICATIONS

Addison, Paul S., The Illustrated Wavelet Transform Handbook, Taylor & Francis Group, 2002.

(Continued)

*Primary Examiner* — L. G Lauchman

(57) ABSTRACT

Techniques for the display of a signal with a wavelet transform of that signal in a wavelet transform viewer are disclosed, according to embodiments. According to embodiments, the wavelet transform viewer can display a plot of physiological signals such as a photoplethysmograph (PPG) signal. A portion of the plot of the signal can be selected. A wavelet transform the selected portion of the signal can be calculated and a wavelet plot of the tranformed signal can be displayed simultaneously with that signal. A plot of the selected portion of the signal can also be simultaneously displayed with both the plot of the signal and the wavelet plot.

21 Claims, 13 Drawing Sheets

U.S. PATENT DOCUMENTS

| | | |
|---|---|---|
| 6,325,761 B1 | 12/2001 | Jay |
| 6,361,501 B1 | 3/2002 | Amano et al. |
| 6,393,311 B1 | 5/2002 | Edgar, Jr. et al. |
| 6,561,986 B2 | 5/2003 | Baura |
| 6,608,934 B2 | 8/2003 | Scheirer |
| 6,654,623 B1 | 11/2003 | Kastle |
| 6,810,277 B2 | 10/2004 | Edgar, Jr. et al. |
| 6,931,269 B2 | 8/2005 | Terry |
| 7,001,337 B2 | 2/2006 | Dekker |
| 7,020,507 B2 | 3/2006 | Scharf |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,515,949 B2 | 4/2009 | Norris |
| 7,519,488 B2 | 4/2009 | Fu |
| 7,523,011 B2 | 4/2009 | Akiyama et al. |
| 2003/0163057 A1 | 8/2003 | Flick et al. |
| 2005/0043616 A1 | 2/2005 | Chinchoy |
| 2005/0070774 A1 | 3/2005 | Addison et al. |
| 2006/0209631 A1 | 9/2006 | Melese et al. |
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0082018 A1 | 4/2008 | Sackner et al. |
| 2008/0214903 A1 | 9/2008 | Orbach |
| 2008/0243021 A1 | 10/2008 | Causevic et al. |

FOREIGN PATENT DOCUMENTS

| | | |
|---|---|---|
| WO | WO 01/25802 | 4/2001 |
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm For The Determination Of Respiratory Rate From The Photoplethysmogram," Journal of Clinical Monitoring and Computing, 2006.

Leonard, Paul A., Clifton, David, Addison, Paul S., Watson, James N., Beattie, Tom "An Automated Algorithm For Determining Respiratory Rate By Photoplethysmogram In Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

Addison P S et al: "Secondary wavelet feature decoupling (SWFD) and its use in detecting patient respiration from the photoplethysmogram" Proceedings of the 25TH. Annual International Conference of the IEEE Engineering in Medicine and Biology Society. Cancun, Mexico, Sep. 17, 2003 0917; 20030917-20030921 New York, NY: IEEE, US, vol. 3, Sep. 17, 2003, pp. 2602-2605, XP010691353 ISBN: 978-0-7803-7789-9 the whole document.

SYSTEMS AND METHODS FOR A WAVELET TRANSFORM VIEWER

CROSS-REFERENCE TO RELATED APPLICATIONS

This application claims the benefit of U.S. Provisional Application No. 61/077,072, filed Jun. 30, 2008 and U.S. Provisional Application No. 61/077,130, filed Jun. 30, 2008, which are hereby incorporated by reference herein in their entireties.

SUMMARY

The present disclosure relates to a signal viewer and, more particularly, the present disclosure relates to a wavelet transform viewer for the simultaneous display of a signal with a wavelet transform of that signal.

In an embodiment, a wavelet transform viewer is provided that can simultaneous display a signal and a wavelet transform of a portion of that signal. A signal is received and a portion of the signal is selected. The selected portion of the signal is transformed using a wavelet transform to generate a transformed signal. A wavelet plot is generated based on the transformed signal and the wavelet plot is displayed with the signal.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
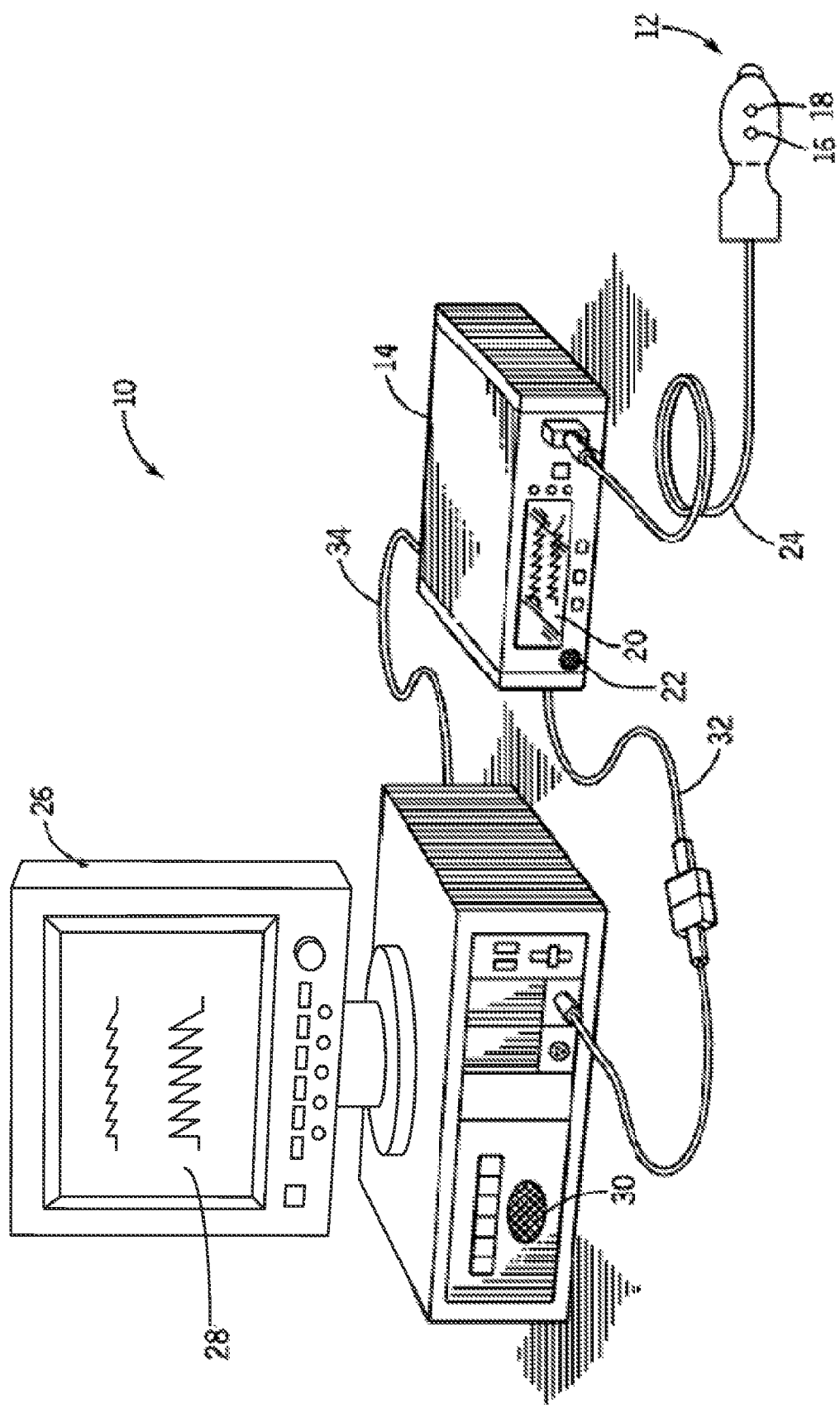
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))l(t)) \quad (1)$$

where:
λ=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "$SpO_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
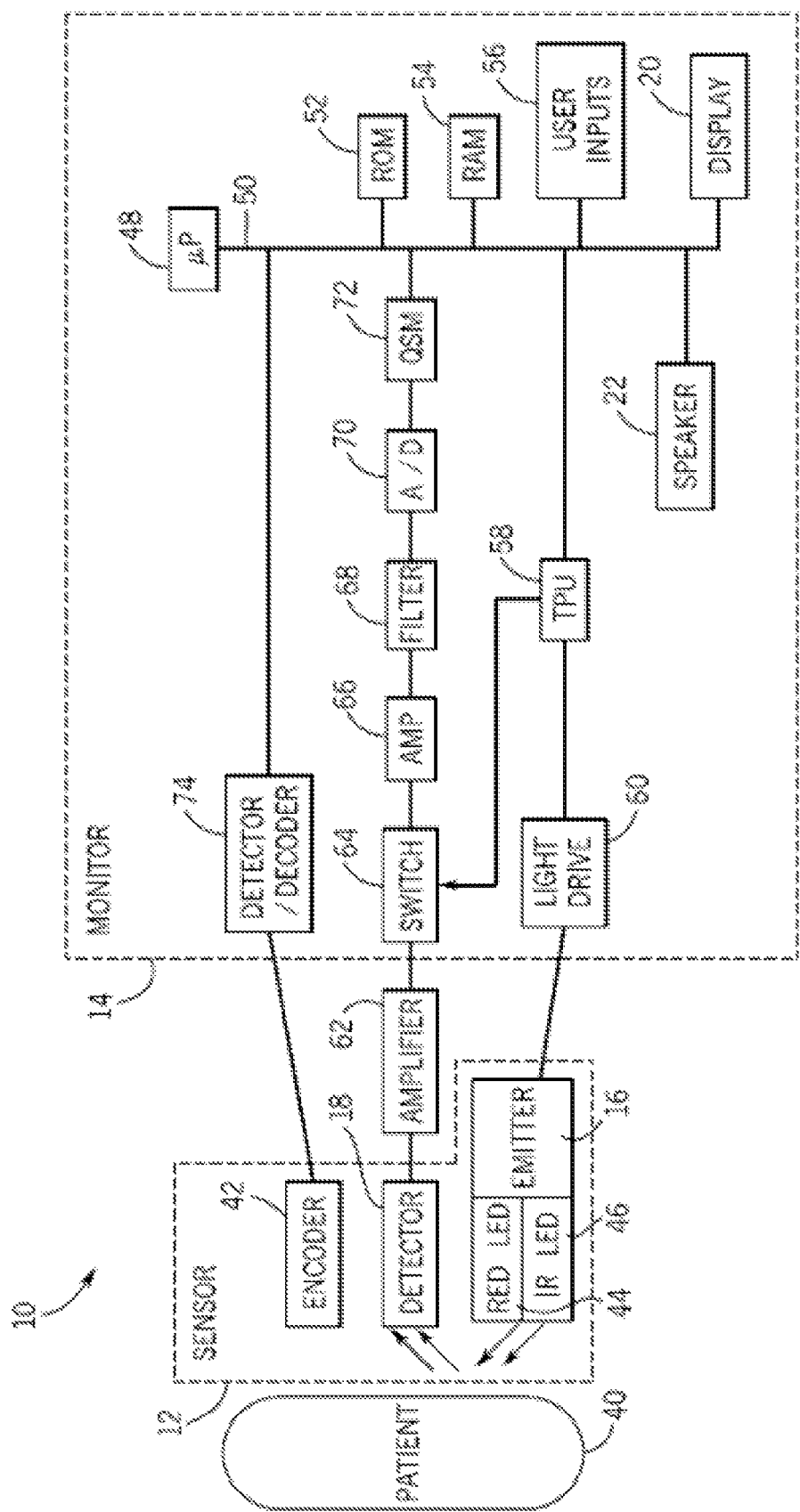
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a,b) = \frac{1}{\sqrt{a}} \int_{-\infty}^{+\infty} x(t)\psi^*\left(\frac{t-b}{a}\right)dt \quad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \qquad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \qquad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
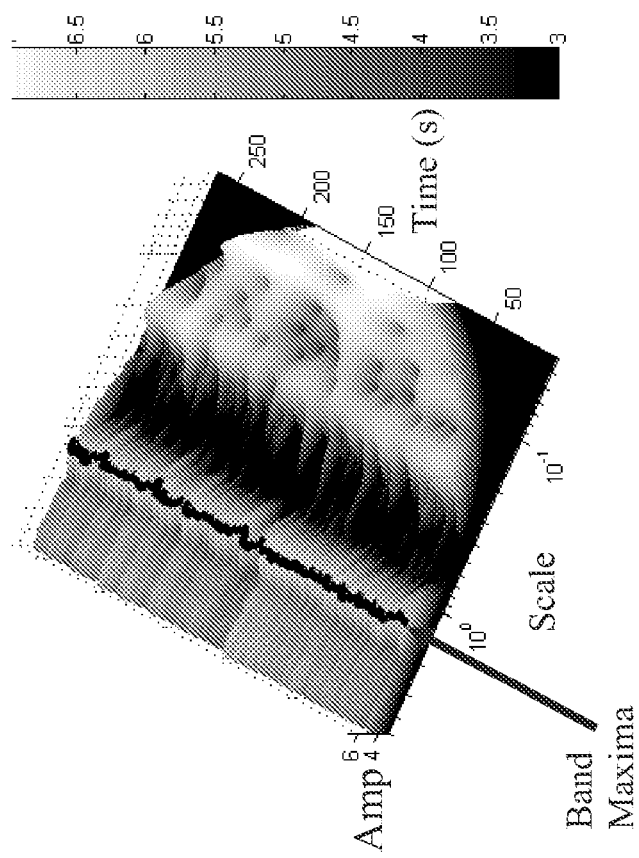
FIGS. 3(a) and 3(b) show illustrative views of a scalogram derived from a PPG signal in accordance with an embodiment.
Figure 3A:
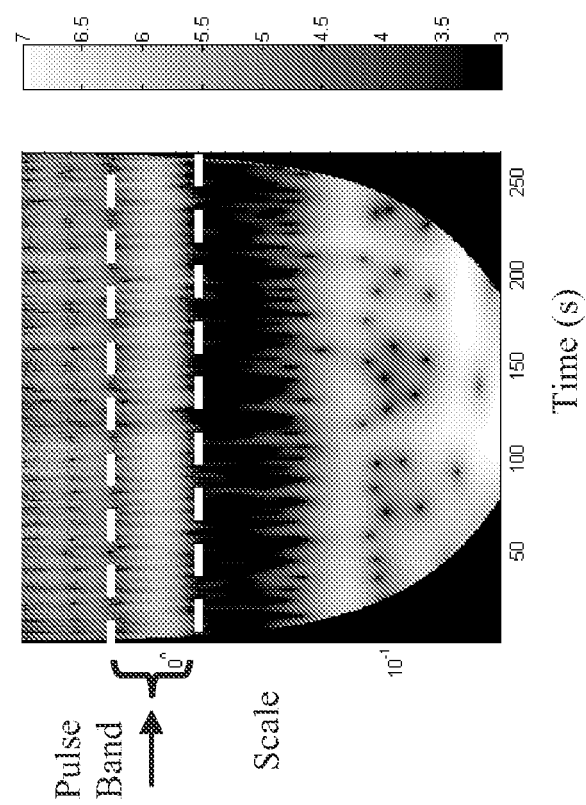

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
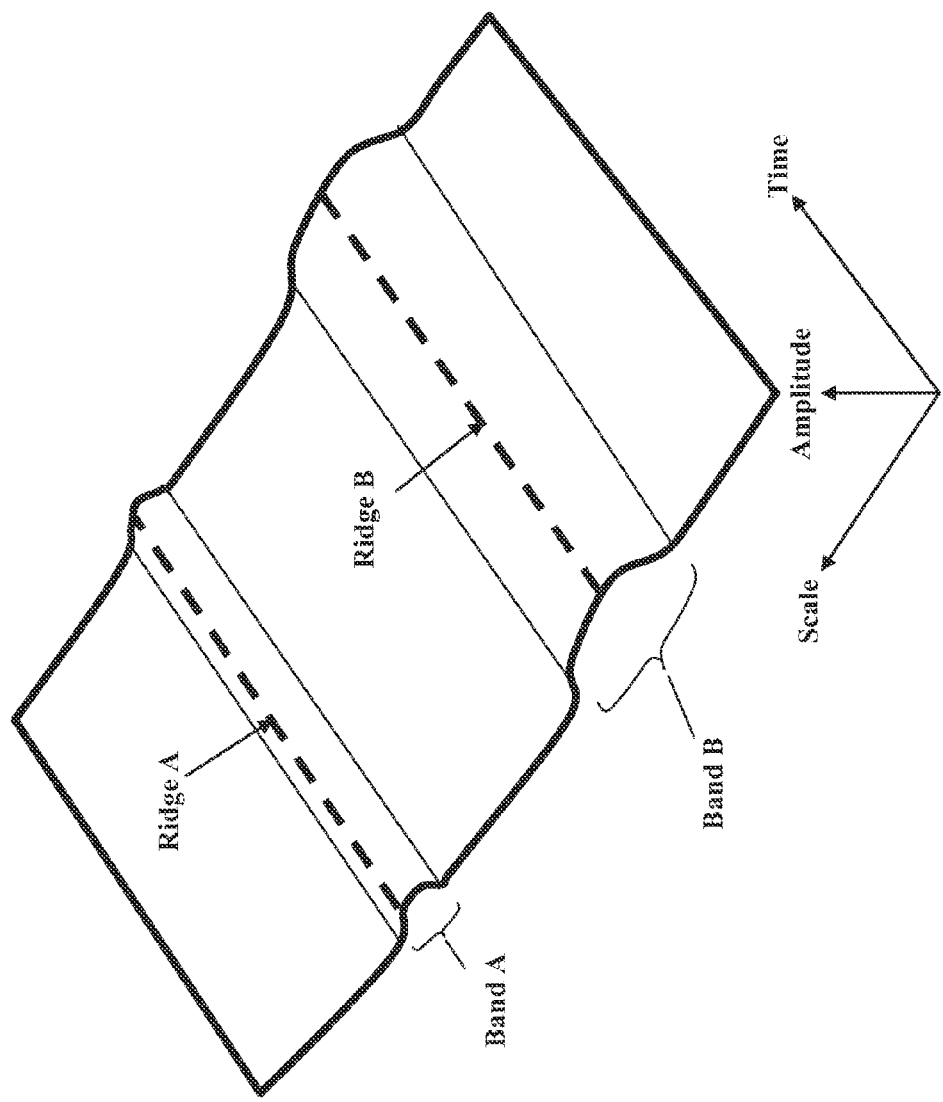
FIG. 3(c) shows an illustrative scalogram derived from a signal containing two pertinent components in accordance with an embodiment.
Figure 3D:
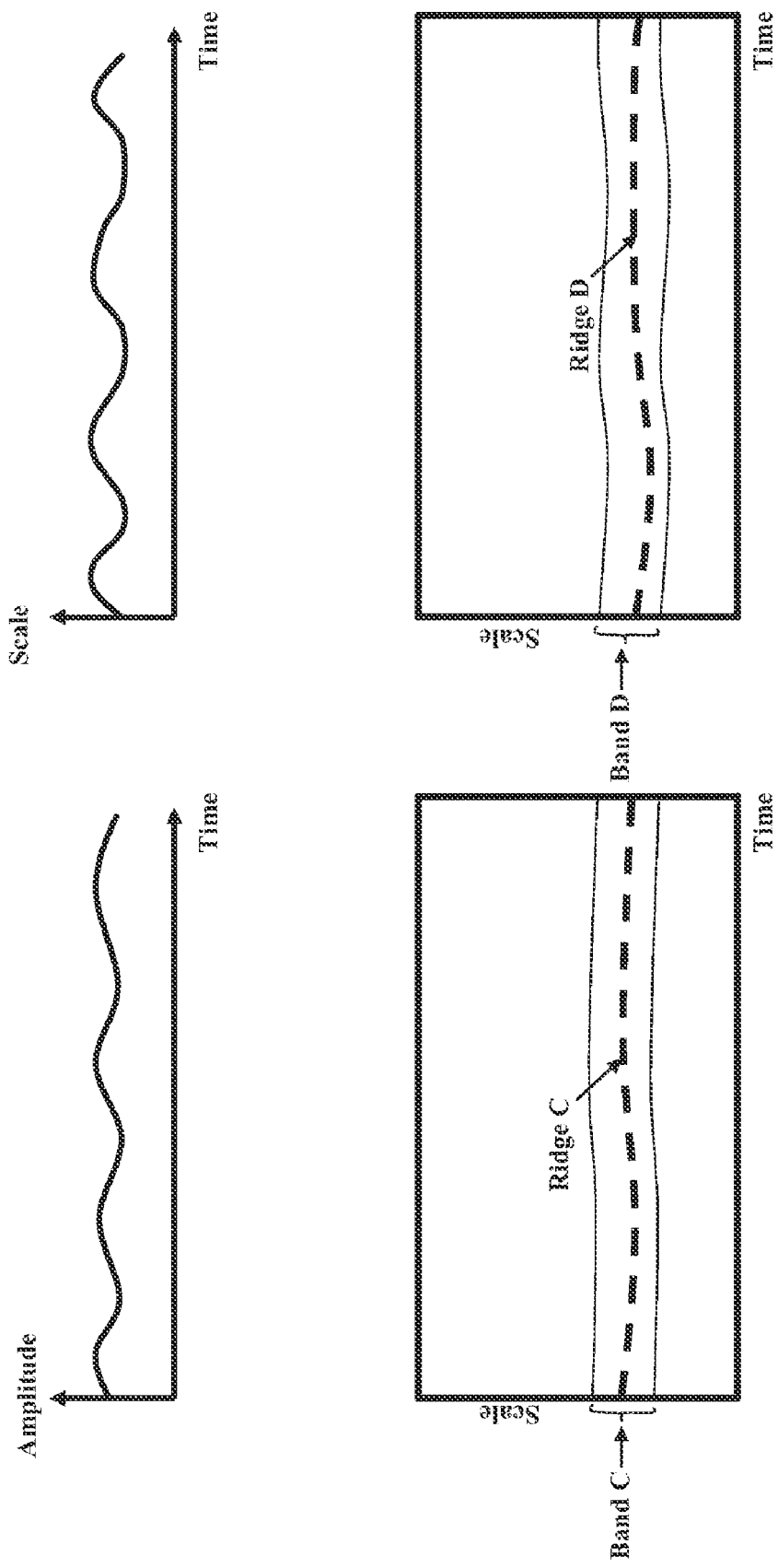
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \qquad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \qquad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \qquad (17)$$

Figure 3E:
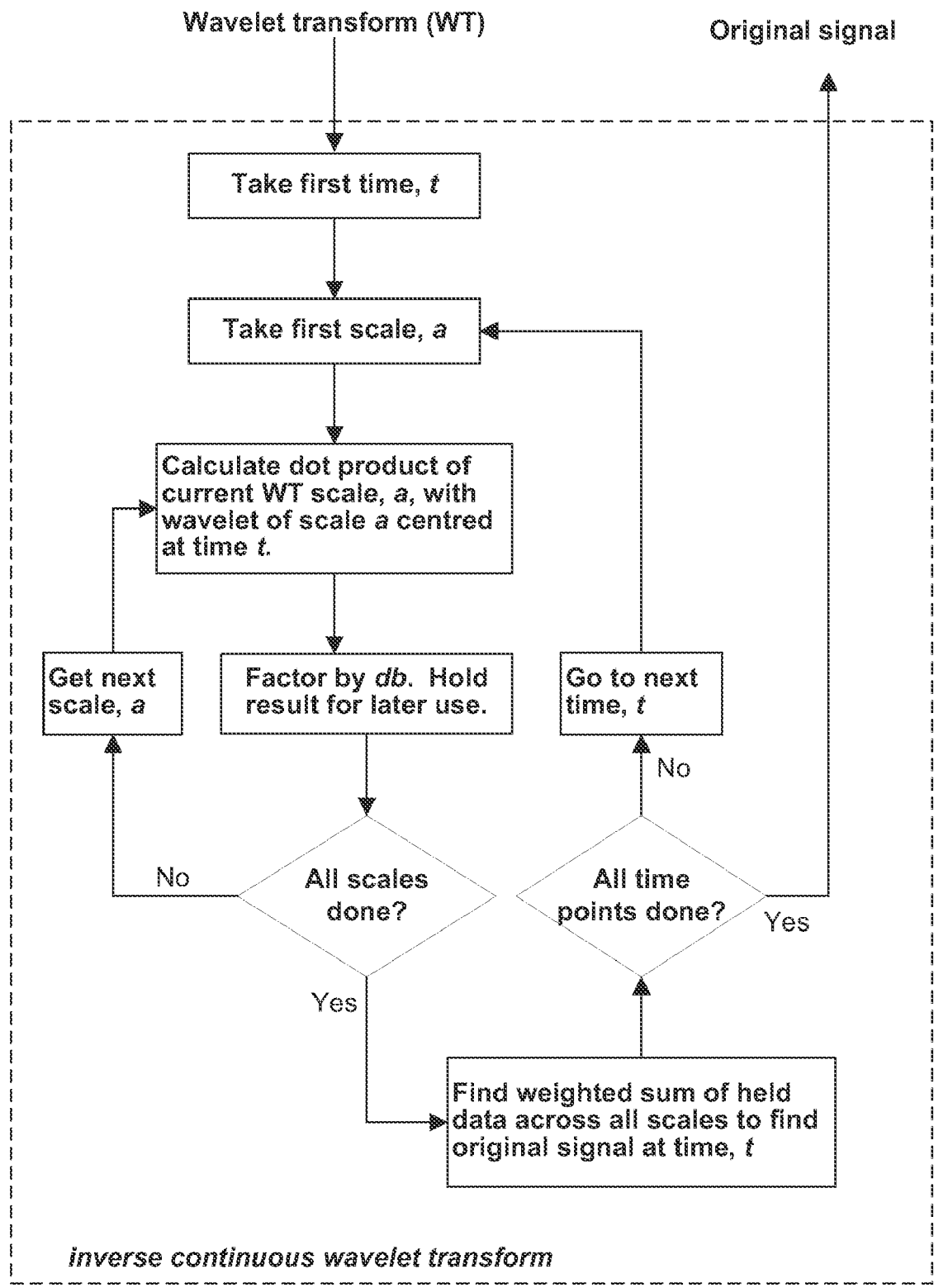
FIGS. 3(e) and 3(f) are flow charts of illustrative steps involved in performing an inverse continuous wavelet transform in accordance with embodiments.
Figure 3F:
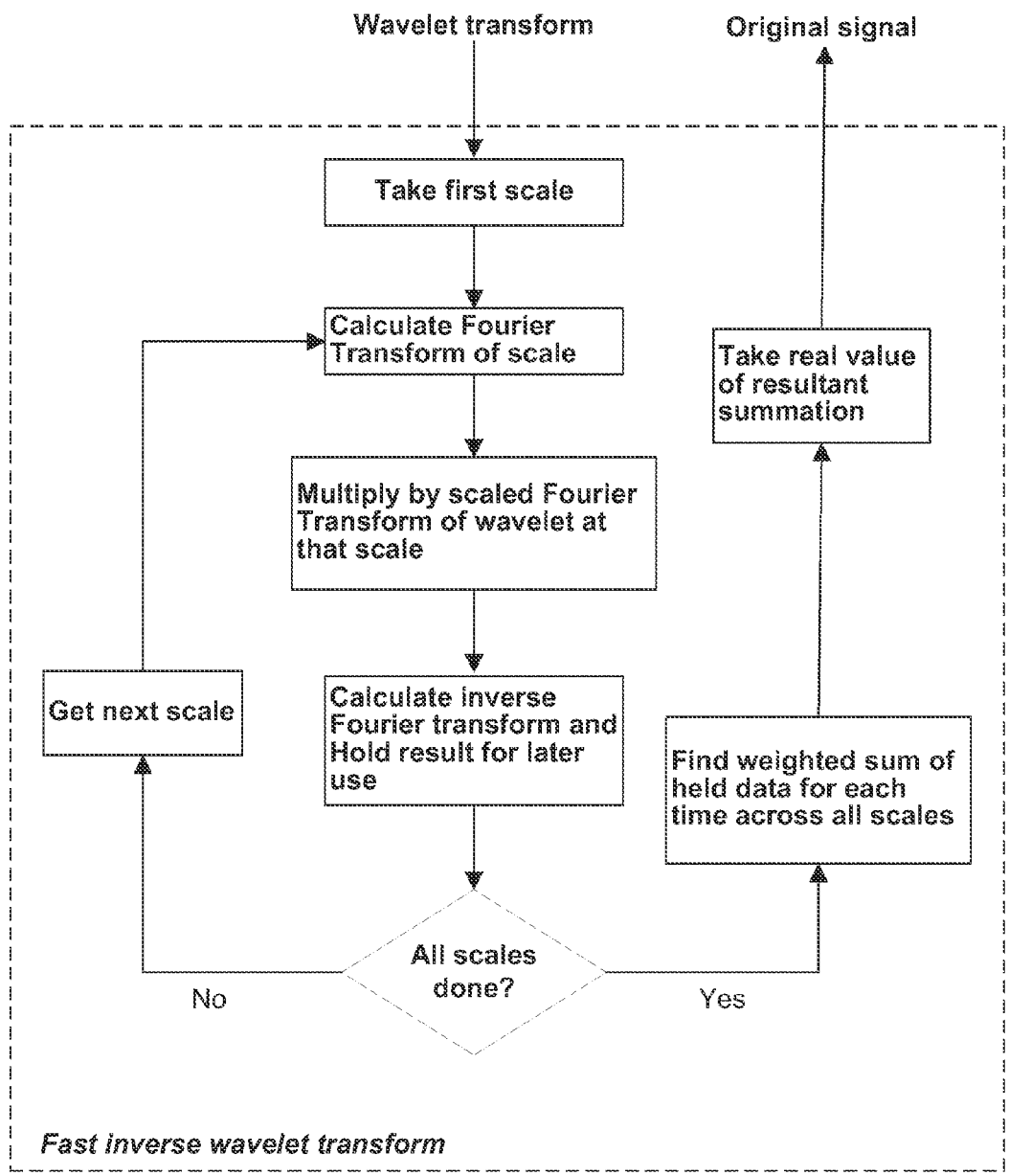

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
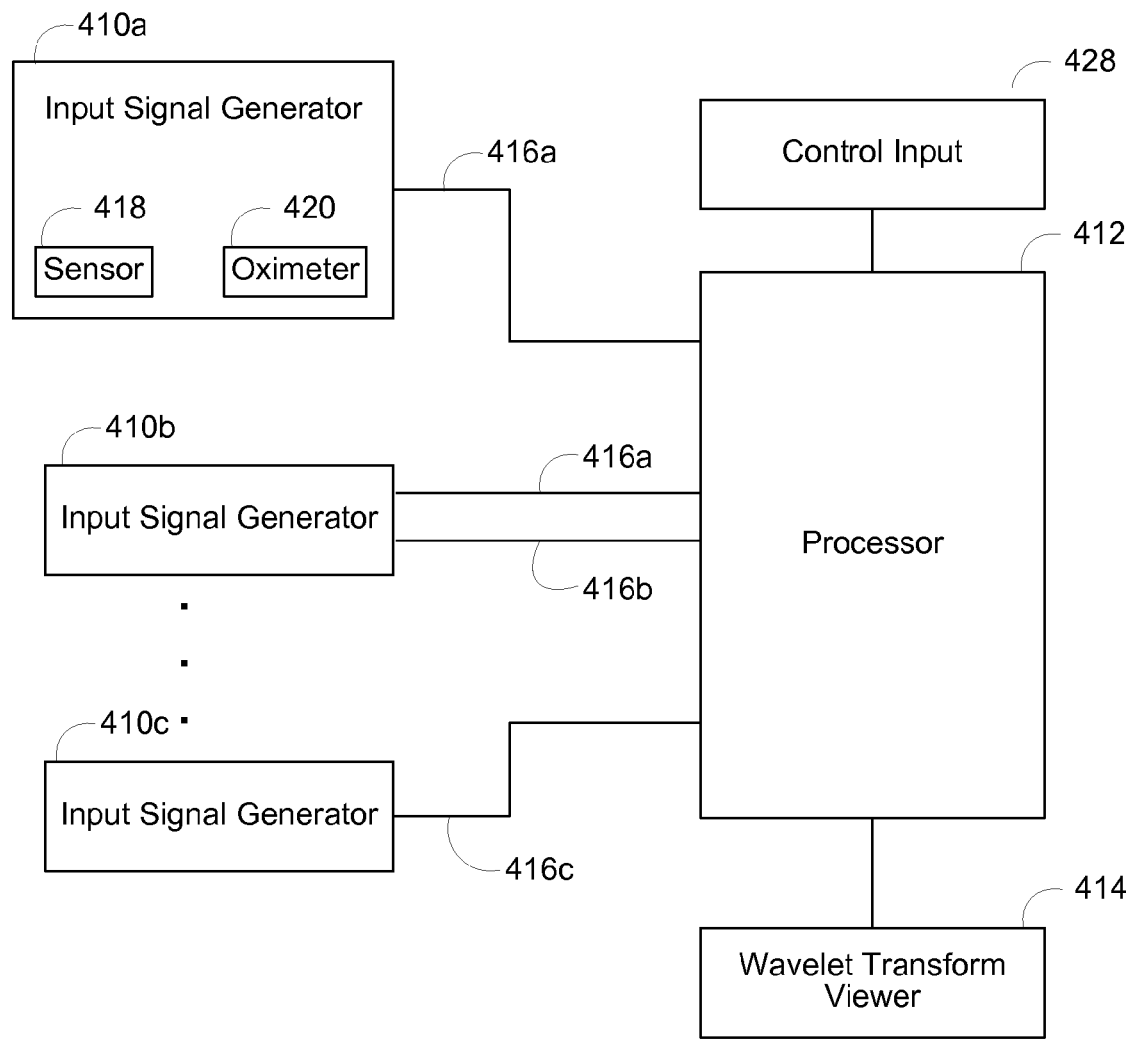
FIG. 4 is a block diagram of an illustrative continuous wavelet processing system that includes a wavelet transform viewer in accordance with some embodiments.

FIG. 4 is an illustrative continuous wavelet processing system 400 that may include a wavelet transform viewer in accordance with some embodiments. In this embodiment, one or more input signal generators 410 each generate one or more input signal 416. As illustrated, input signal generator 410a may include oximeter 420 coupled to sensor 418, which may provide as input signal 416a, a PPG signal. It will be understood that input signal generators 410 may include any suitable signal sources, signal generating data, signal generating equipment, or any combination thereof to produce signals 416. Signals 416 may be any suitable signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal and/or any combination thereof.

In this embodiment, signals 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signals 416 to filter signals 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signals 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to wavelet transform viewer 414. Wavelet transform viewer 414 may be integrated with or used in combination with any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, an input signal generator 410 may be implemented as parts of sensor 12 and monitor 14 and processor 412 may be implemented as part of monitor 14.

Control input 428 may be coupled to processor 412 and may be used to control the operation of processor 412 and wavelet transform viewer 414. In some embodiments control input 428 may be coupled directly to wavelet transform viewer 414 (not shown). Control input 428 may be any suitable user interface, such as a remote control, mouse, trackball, keypad, keyboard, touch screen, touch pad, stylus input, joystick, voice recognition interface, or other user input interfaces.

The present disclosure relates to a wavelet transform viewer for displaying signals, such as physiological signals (e.g., a PPG signal) simultaneously with a wavelet plot of at least one of those signals. For example, the wavelet transform viewer may simultaneously display a PPG signal and a wavelet transform generated from the PPG signal. The wavelet transform viewer may allow a particular portion of the physiological signal to be selected such that the displayed wavelet transform can be generated for the selected portion of the physiological signal. This selected portion may be an area of interest on the physiological signal and thus the wavelet transform scalogram generated from this selected area may provide additional information relating to the area of interest.

The wavelet transform viewer may be part of a physiological monitoring system (e.g., a PSG) that can simultaneously display multiple physiological signals and physiological parameters including, for example, ECG signals, EEG signals, EOG signal, and EMG signals. These signals may be displayed within the viewer simultaneously with at least one wavelet plot generated from a selected portion of one of the signals.

Figure 5:
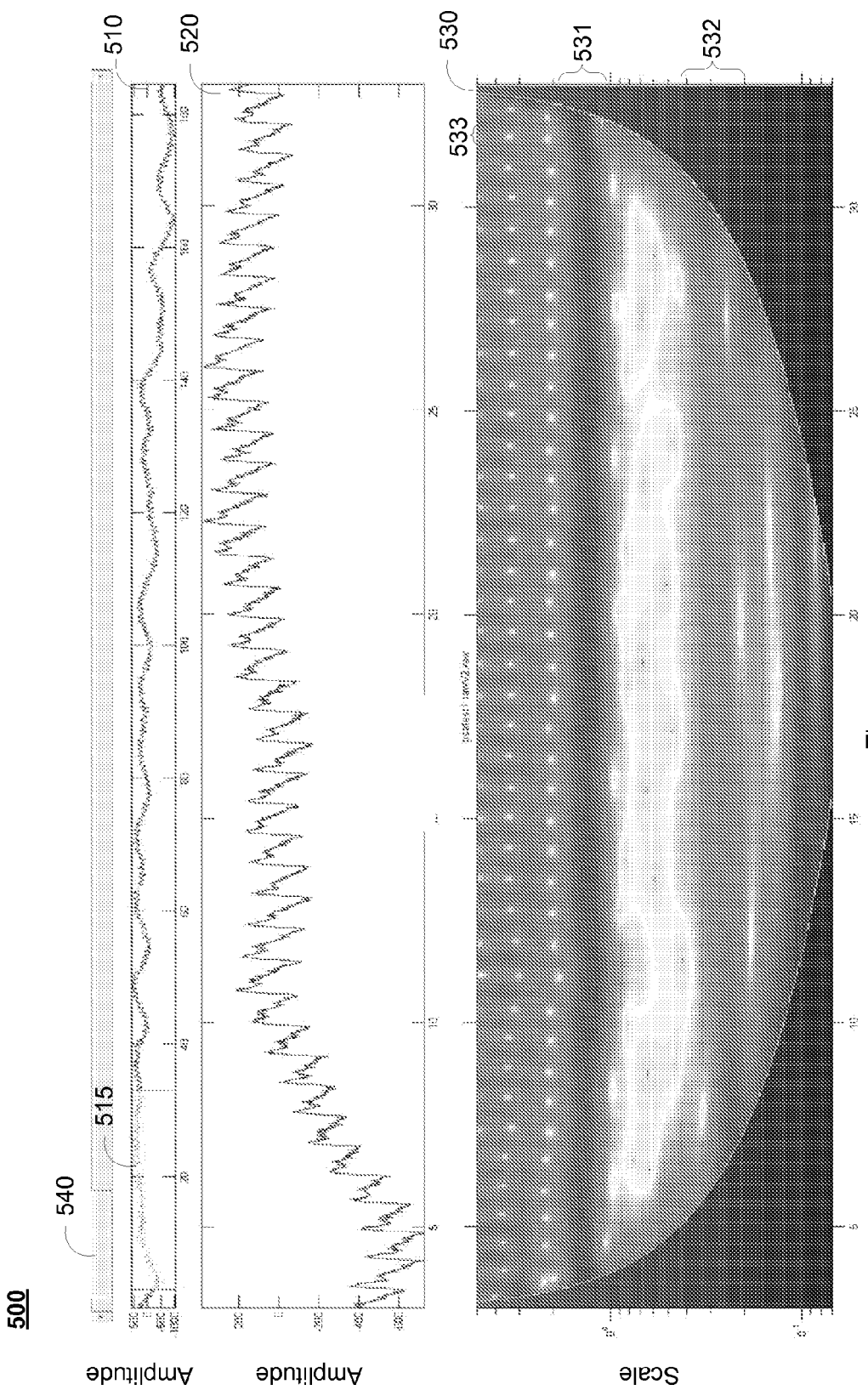
FIGS. 5-8 are illustrative displays of a wavelet transform viewer in accordance with embodiments.

FIG. 5 shows an illustrative display 500 of a wavelet transform viewer in accordance with embodiments. Display 500 includes large signal plot 510 of a signal plotted over time. The signal may be a PPG signal or any other suitable signal. Selection box 515 may be used to select a portion of the signal from large signal plot 510. Selected signal plot 520 is a plot of the selected portion of the signal. Wavelet plot 530 is a plot of a wavelet transform generated from the selected portion of the signal. In some embodiments, wavelet plot 530 may be a wavelet scalogram plot. Wavelet plot 530 may include pulse band 531, respiration band 532, and individual pulse features 533. In particular, the pulse may be shown as band 531 across the scalogram in the modulus plot with individual pulse features 533 becoming apparent at smaller scales as the wavelet transform resolves the intra-pulse morphology at these scales.

Figure 6:
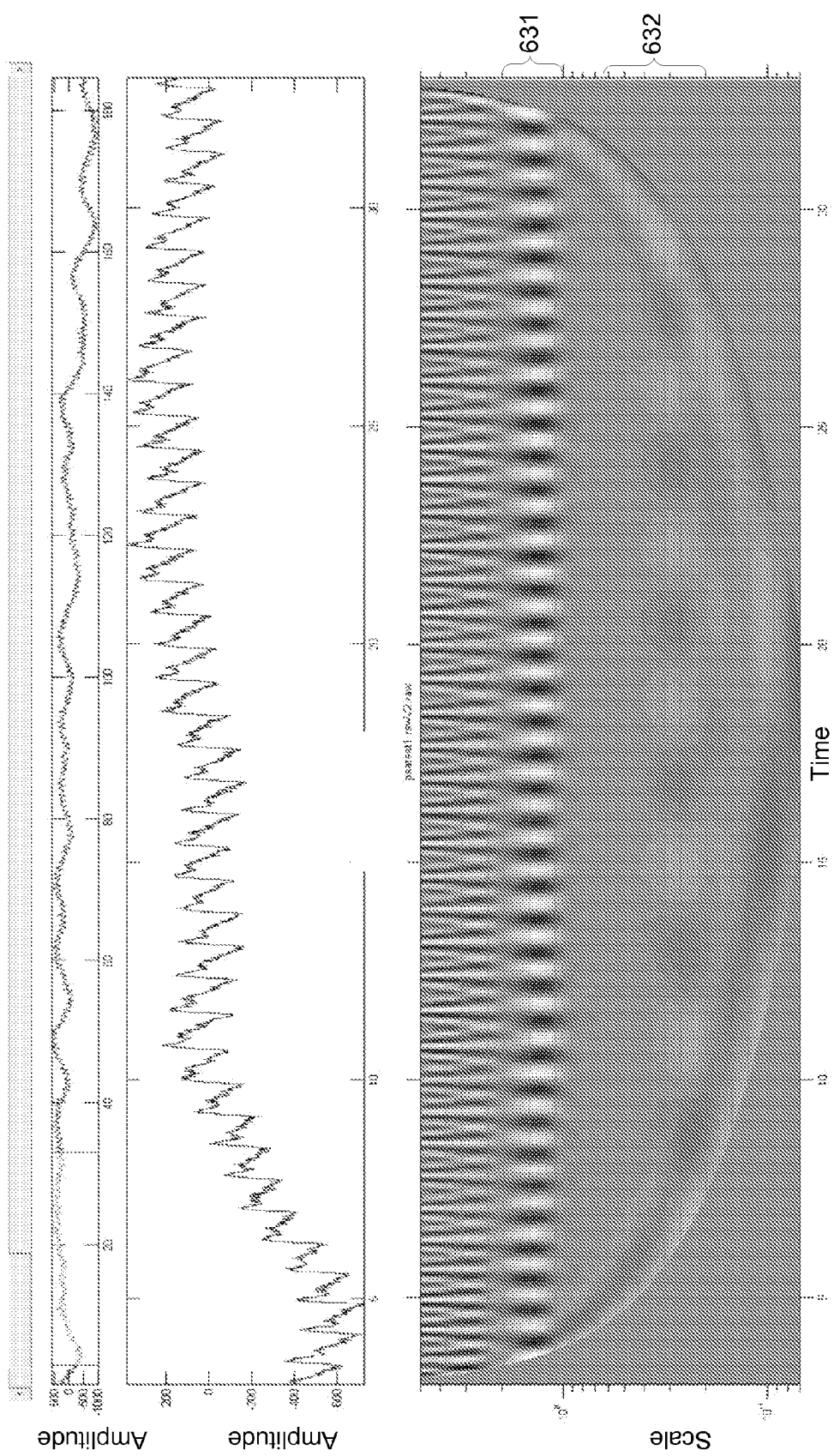
Figure 7:
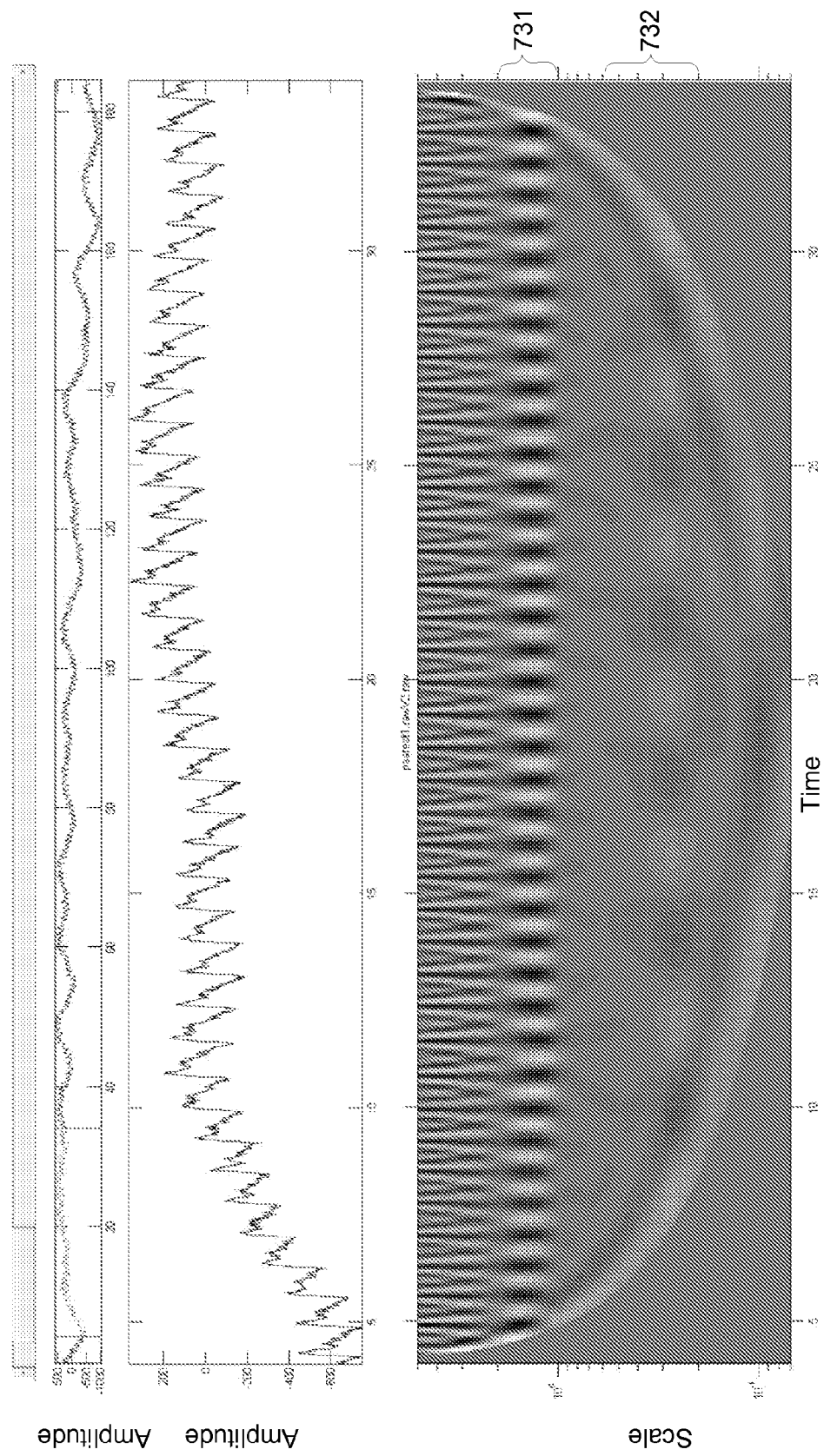
Figure 8:
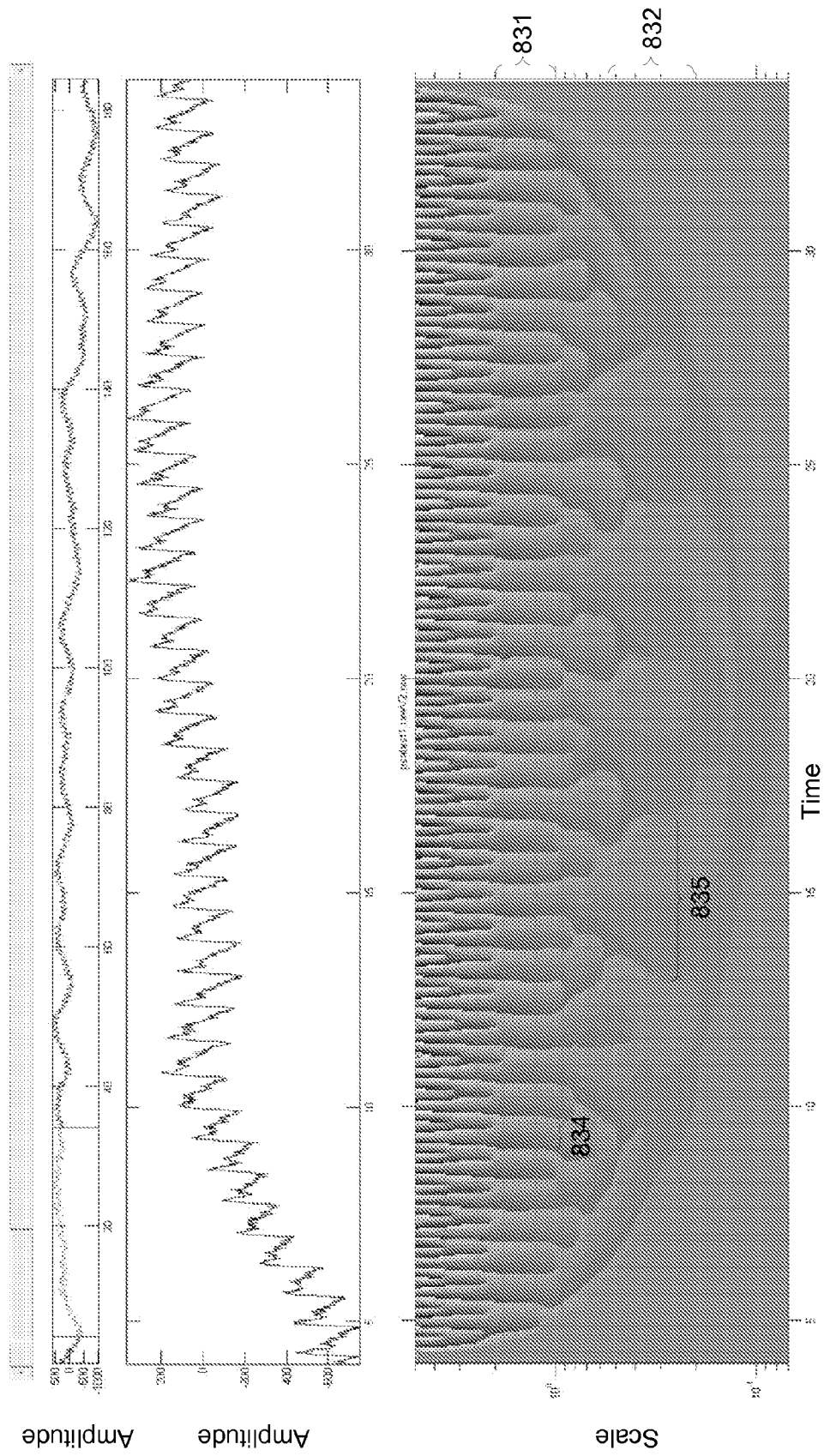

In addition to a scalogram plot of the wavelet transform modulus values (and multiples thereof), other wavelet transform plots can be provided in the wavelet transform viewer including the phase of the transform, real or imaginary parts of the transform, and cross-correlations between the signal and other signals and their transforms. For example, FIG. 6 shows an illustrative wavelet transform viewer that includes a wavelet transform plot of the real parts of the transform with pulse band 631 and respiration band 632, FIG. 7 shows an illustrative wavelet transform viewer that includes a wavelet transform plot of the imaginary parts of the transform with pulse band 731 and respiration band 732, and FIG. 8 shows an illustrative wavelet transform viewer that includes a wavelet transform plot of the phase of the transform with pulse band 831, respiration band 832, pulse cycle "beat period" 834, and respiration cycle "breath period" 835 in accordance with embodiments. The real and imaginary transform plots (FIGS. 6-7) may show the oscillatory nature of the pulse and features. In addition, the cycling of respiratory activity can be see at lower scales. The phase plot (FIG. 8) also shows the regular cycling of phase at the pulse and respiratory scales. The regular cycling of the pulse and respiratory activity are indicative of the heart beat period and breath period respectively. The phase plot is also useful in visualizing marked changes in phase relationships within the signal.

Returning to FIG. 5, the time scale of selected signal plot 520 may be smaller than the time scale of large signal plot 510. In other words, large signal plot 510 may display the signal over a relatively longer time period and selected signal plot 520 may show the selected portion of the signal over a relatively shorter time period. Displaying the selected portion of the signal in this manner may allow the selected portion of the signal to be viewed and examined in greater detail within selected signal plot 520 than within large signal plot 510. Selected signal plot 520 and wavelet plot 530 may be displayed with substantially similar time scales and may correspond to approximately the same selected portion of the signal.

Wavelet plot 530 may also aid in signal interpretation. As discussed above, computing a wavelet transform of the signal and displaying a wavelet plot of the transformed signal may reveal information that may not be readily observed from the signal itself. For example, a scalogram of a selected portion of a PPG signal may provide pulse and other heart rate information. As another example, a scalogram of a selected portion may provide respiratory information such as respiration rate, respiration effort, and changes in respiratory activity. Such respiration activity as interpreted from the wavelet transform plot may aid in the diagnosis of, for example, apnea type. As yet another example, a scalogram of a selected portion may provide information on large scale signal artifact due to, for example, movement or vasomotion. Vasomotion may, for example, be indicative of sleep arousal.

According to embodiments, if an area of interest is identified within large signal plot 510, the area can be selected using selection box 515. The selected portion of the signal may then be simultaneously displayed in selected signal plot 520 and wavelet plot 530. Selection box 515 may select any portion of large signal plot 510, including portions of large signal plot that are out of the range of the viewer. Selection box may be moved along the time axis of large signal plot using selection slider 540. Selection slider 540 may be moved left and right using any suitable user interface such as control input 428 (FIG. 4). Similarly, control input 428 also may be used to directly select a particular portion of large signal plot 510. Finally, control input 428 may also be used to input a time that may approximately correspond to a desired start-point, end-point, or mid-point for selection box 515. Additionally, automated selection of portion to be viewed may be achieved by, for example, automatically zooming into identified regions of interest (e.g., areas of apnea).

The size of selection box 515 may also be adjusted to set the size or time span of the signal portion to be selected. For example, the size of selection box 515 may be increased or decreased by selecting and moving either of the edges of selection box 515 using control input 428. A larger period may be selected when viewing longer period events or sequence of events and shorter periods may be selected when viewing temporally localized events. Alternatively, control input 428 may be used to select the size or time span of selection box 515 from several pre-determined sizes or may be used to enter a desired size or time span.

After the portion of the signal is selected, a wavelet transform of the selected portion of the signal may be calculated and a wavelet plot may be generated from the transformed signal. When the selection is changed or adjusted, a new wavelet transform may be computed and a new wavelet plot may be generated. Wavelet transforms may be calculated for an entire signal. However, signals tend to be very long and it may be very computationally expensive to perform a high resolution wavelet transform on an entire signal. Therefore, in accordance with embodiments, the wavelet transform may be calculated after a signal portion is selected and the resolution of the transform may be optimized accordingly (e.g., by sub-sampling the sampling time and scales as appropriate for viewing purposes).

Although only one signal (e.g., a PPG signal) is shown in display 500, it should be understood that wavelet transform viewer 414 may support the simultaneous display of multiple signals. For example, wavelet transform viewer 414 may be used to display the output of a polysomnograph (PSG) for use in monitoring a group of physiological changes that occur during sleep. A PSG typically monitors PPG signals, EEG signals, ECG signals, EOG signal, EMG signals, and any other suitable signal. Some or all of these monitored signals may be simultaneously displayed in wavelet transform viewer 414. The monitored signals may be simultaneously displayed on individual large signal plots or grouped together in several large scale plots with some signals being plotted on the same set of axes.

When multiple signals are displayed within wavelet transform viewer 414 one or more selected signal plots and wavelet plots may be simultaneously displayed. In some embodiments only one selected signal plot and one wavelet plot are displayed. The selected signal plot and the wavelet plot may correspond to a particular signal (e.g., a PPG signal) or may be configured to correspond to any of several signals. For example, the selected signal and wavelet plots may be set to correspond to either a PPG signal or an EEG signal. Alternatively, multiple selected signal plots and wavelet plots may be provided for the simultaneous display of multiple signals. In some embodiments, one or more of the wavelet plots may be displayed without a corresponding selected signal plots. This may free space within wavelet transform viewer 414 for additional signal and wavelet plots.

Figure 9:
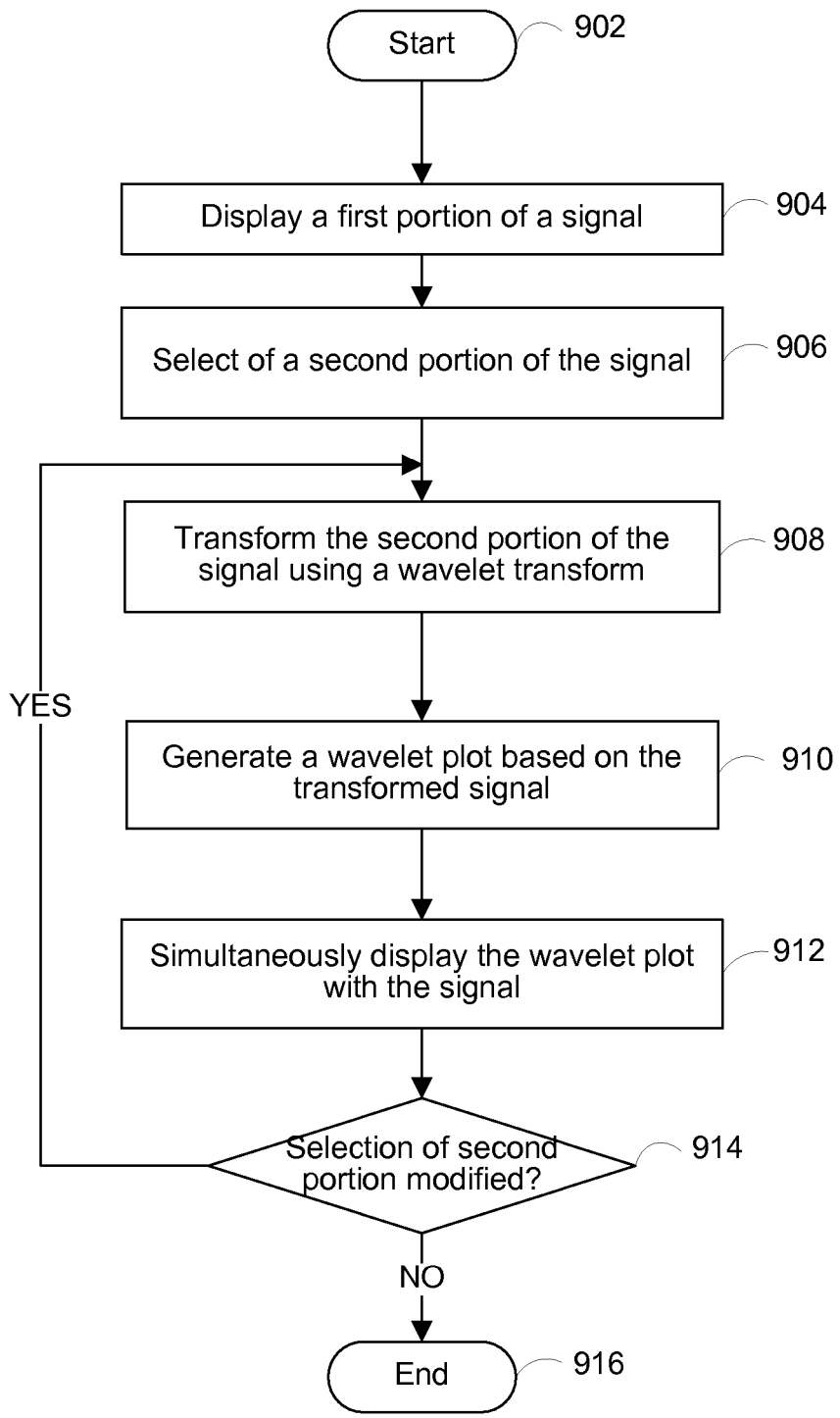
FIG. 9 flowchart of an illustrative process for generating a wavelet transform viewer display in accordance with an embodiment.

FIG. 9 is a flowchart of an illustrative process for generating a wavelet transform viewer display in accordance with an embodiment. Process 900 may begin at step 902. At step 904, a first portion of a signal is displayed. For example, the first portion of the signal may be displayed within large signal plot 510 of FIG. 5. The signal may be a PPG signal, another physiological signal, or any other suitable signal. At step 906, a second portion of the signal is selected. In an embodiment, the second portion of the signal may selected from within the first portion of the signal. The location and size of the second portion of the signal may be adjustable. The selection may be made manually using control input 428 or automatically using processor 412 (FIG. 4).

Process 900 may advance to step 908, in which the second portion of the signal is transformed using a wavelet transform. At step 910 a wavelet plot is generated based on the transformed signal. The wavelet plot may be a wavelet scalogram as show in FIG. 5 or may be a wavelet plot that is based on any other suitable wavelet transform including the phase of the transform, real or imaginary parts of the transform, and cross-correlations between the signal and other signals and their transforms. Then, at step 912 the wavelet plot is simultaneously displayed with the signal. The wavelet plot may be simultaneously displayed with the first portion of the signal, with the second portion of the signal or with any suitable portion of the signal. As show in FIG. 5, the wavelet plot may simultaneously displayed with both the first and the second portion of the signal.

Process 900 may then advance to step 914, to determine whether the selection of the second portion has been modified. The selection of the second portions may be modified in order to display a wavelet plot of a different portion of the signal. The selection of the second portion may also be modified in order to adjust the current selection, for example, by adjusting the start point, end point, or duration of the selection. The modification may be made manually using control input 428 or automatically using processor 412 (FIG. 4). If the second portion has been modified, steps 908-914 may be repeated to transform the modified portion, generate a wavelet plot based on the transformed signal, and simultaneously display the wavelet plot with the signal. If the second portion has not been modified, process 900 may then advance to step 916 and end.

The foregoing is merely illustrative of the principles of this disclosure and various modifications can be made by those skilled in the art without departing from the scope and spirit of the disclosure. The following claims may also describe various aspects of this disclosure.

What is claimed is:

1. A method for displaying a signal in a wavelet transform viewer, the method comprising:
    receiving a signal in a processor;
    receiving a user selection of a portion of the signal corresponding to an area of interest via control input;
    transforming the selected portion of the signal using a wavelet transform using the processor to generate a transformed signal;

generating a wavelet plot based on the transformed signal using the processor; and displaying the wavelet plot simultaneously with a plot of the selected portion of the signal on a display.

2. The method of claim 1 wherein the signal comprises a photoplethysmographic (PPG) signal.

3. The method of claim 1 wherein the wavelet plot comprises a continuous wavelet scalogram of the transformed signal.

4. The method of claim 1 wherein the wavelet plot comprises a plot of a phase of the transformed signal, a real part of the transformed signal, an imaginary part of the transformed signal, and/or a cross-correlation between the transformed signal and a second signal, and/or combinations thereof.

5. The method of claim 1 wherein the selected portion of the signal is adjustable.

6. The method of claim 1 further comprising displaying a plot of the received signal simultaneously with the plot of the selected portion of the signal and the wavelet plot.

7. The method of claim 1 further comprising:
receiving a selection of a second portion of the signal;
transforming the selected second portion of the signal using a wavelet transform to generate a further transformed signal;
regenerating the wavelet plot based on the further transformed signal; and
replacing the displayed wavelet plot with the regenerated wavelet plot.

8. The method of claim 1 further comprising displaying at least one other signal plot with the wavelet plot and the plot of the selected portion of the signal.

9. The method of claim 1 further comprising displaying a wavelet plot of at least one other signal.

10. The method of claim 1 further comprising displaying the wavelet plot with the plot of the selected portion of the signal within a polysomnograph (PSG) display.

11. A wavelet transform viewer comprising:
a processor capable of:
receiving a signal;
receiving a user selection of a portion of the signal corresponding to an area of interest;
transforming the selected portion of the signal using a wavelet transform to generate a transformed signal;
generating a wavelet plot based on the transformed signal; and
a display capable of displaying the wavelet plot simultaneously with a plot of the selected portion of the signal.

12. The wavelet transform viewer of claim 11 wherein the signal comprises a photoplethysmographic (PPG) signal.

13. The wavelet transform viewer of claim 11 wherein the wavelet plot comprises a continuous wavelet scalogram of the transformed signal.

14. The wavelet transform viewer of claim 11 wherein the wavelet plot comprises a plot of a phase of the transformed signal, a real part of the transformed signal, an imaginary part of the transformed signal, and/or a cross-correlation between the transformed signal and a second signal, and/or combinations thereof.

15. The wavelet transform viewer of claim 11 further comprising a control input capable of selecting and/or adjusting the selected portion of the signal.

16. The wavelet transform viewer of claim 11 wherein the display is further capable of displaying a plot of the received signal with the plot of the selected portion of the signal and the wavelet plot.

17. The wavelet transform viewer of claim 11 the processor further capable of:
receiving a selection of a second portion of the signal;
transforming the selected second portion of the signal using a wavelet transform to generate a further transformed signal;
regenerating the wavelet plot based on the further transformed signal; and
replacing the displayed wavelet plot with the regenerated wavelet plot.

18. The wavelet transform viewer of claim 11 wherein the display is further capable of displaying at least one other signal plot with the wavelet plot and the plot of the selected portion of the signal.

19. The wavelet transform viewer of claim 11 wherein the display is further capable of displaying a wavelet plot of at least one other signal.

20. The wavelet transform viewer of claim 11 wherein the display comprises a polysomnograph (PSG) display.

21. Computer-readable medium for use in displaying a signal in a wavelet transform viewer, the computer-readable medium having computer program instructions recorded thereon for:
receiving a signal;
receiving a user selection of a portion of the signal corresponding to an area of interest;
transforming the selected portion of the signal using a wavelet transform to generate a transformed signal;
generating a wavelet plot based on the transformed signal; and
displaying the wavelet plot simultaneously with a plot of the selected portion of the signal.

* * * * *